U S009261353B2

United States Patent
Sang et al.

(10) Patent No.: US 9,261,353 B2
(45) Date of Patent: Feb. 16, 2016

(54) MEDICAL ROBOTIC SYSTEM INCLUDING SURGICAL INSTRUMENT POSITION DETECTION APPARATUS AND CONTROL METHOD THEREOF

(71) Applicant: SAMSUNG ELECTRONICS CO., LTD., Suwon-si, Gyeonggi-do (KR)

(72) Inventors: Tae Jun Sang, Suwon-si (KR); Kwang Kyu Lee, Yongin-si (KR); Woong Kwon, Seongnam-si (KR); Kyung Shik Roh, Seongnam-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 317 days.

(21) Appl. No.: 13/728,223

(22) Filed: Dec. 27, 2012

(65) Prior Publication Data

US 2013/0172908 A1 Jul. 4, 2013

(30) Foreign Application Priority Data

Dec. 29, 2011 (KR) ........................ 10-2011-0145455

(51) Int. Cl.
*G06F 19/00* (2011.01)
*G01B 11/14* (2006.01)
(Continued)

(52) U.S. Cl.
CPC ............ *G01B 11/14* (2013.01); *A61B 17/3403* (2013.01); *A61B 17/3494* (2013.01);
(Continued)

(58) Field of Classification Search
CPC ..................... A61B 17/3403; A61B 2017/348; A61B 17/3494; A61B 19/2203; A61B 2019/2211; A61B 2019/2223; A61B 2019/2296; A61B 19/30; A61B 2019/301; A61B 2019/303; A61B 19/5244; A61B 2019/5255; A61B 5/06; A61B 5/065

USPC ........... 700/250, 259, 264, 245; 604/20, 264; 600/114, 117, 118, 424; 606/130
See application file for complete search history.

(56) References Cited

U.S. PATENT DOCUMENTS 4,949,972 A * 8/1990 Goodwin et al. ............. 273/371
5,382,885 A 1/1995 Salcudean et al.
(Continued)

FOREIGN PATENT DOCUMENTS

EP 1815950 A1 8/2007
EP 2014218 1/2009
(Continued)

OTHER PUBLICATIONS

Mansur, "Bored Surgenons Play Game of operation With $1 Mil+ Surgical Robot", Business Insider, Wonderhowto, Apr. 8, 2011, http://www.businessinsider.com/bored-surgeons-play-game-of-operation-with-1-mil-surgical-robot-2011-4.*
(Continued)

*Primary Examiner* — Thomas G Black
*Assistant Examiner* — Sze-Hon Kong
(74) *Attorney, Agent, or Firm* — Harness, Dickey & Pierce, P.L.C.

(57) ABSTRACT

A medical robot system and a method to control the medical robot system are used to detect position information of a surgical instrument in an incised region, thereby improving the safety of robotic surgery. A surgical instrument may be inserted in a through-hole of a trocar inserted into an incised region of a patient. The medical robotic system includes a surgical instrument position detection apparatus to detect position information of the surgical instrument in the through-hole of the trocar, when the surgical instrument is inserted into the through-hole. The medical robotic system further includes a console to control an operation of a surgical robot having the surgical instrument, based on the detected position information of the surgical instrument.

21 Claims, 7 Drawing Sheets

(51) Int. Cl.
  *A61B 19/00* (2006.01)
  *A61B 17/34* (2006.01)

(52) U.S. Cl.
  CPC ......... *A61B19/2203* (2013.01); *A61B 19/5244* (2013.01); *A61B 19/30* (2013.01); *A61B 2017/348* (2013.01); *A61B 2017/3445* (2013.01); *A61B 2019/202* (2013.01); *A61B 2019/2211* (2013.01); *A61B 2019/2296* (2013.01); *A61B 2019/4857* (2013.01); *A61B 2019/5231* (2013.01); *A61B 2019/5255* (2013.01); *A61B 2019/5257* (2013.01); *A61B 2019/5272* (2013.01)

(56) References Cited

U.S. PATENT DOCUMENTS

| | | | | |
|---|---|---|---|---|
| 5,767,839 | A * | 6/1998 | Rosenberg | 345/161 |
| 5,876,325 | A * | 3/1999 | Mizuno et al. | 600/102 |
| 5,988,645 | A * | 11/1999 | Downing | 273/348 |
| 6,491,702 | B2 * | 12/2002 | Heilbrun et al. | 606/130 |
| 6,547,782 | B1 * | 4/2003 | Taylor | 606/14 |
| 6,772,053 | B2 * | 8/2004 | Niemeyer | 700/302 |
| 7,824,417 | B2 * | 11/2010 | Magnusson et al. | 606/130 |
| 8,108,072 | B2 * | 1/2012 | Zhao et al. | 700/250 |
| 8,452,447 | B2 * | 5/2013 | Nixon | 700/245 |
| 8,792,688 | B2 * | 7/2014 | Unsworth | 382/128 |
| 8,792,963 | B2 * | 7/2014 | Zhao et al. | 600/424 |
| 2002/0156345 | A1 * | 10/2002 | Eppler et al. | 600/114 |
| 2005/0085718 | A1 * | 4/2005 | Shahidi | 600/424 |
| 2007/0156019 | A1 | 7/2007 | Larkin et al. | |
| 2008/0146935 | A1 | 6/2008 | Liu | |
| 2008/0275406 | A1 * | 11/2008 | Smith | 604/256 |
| 2009/0234223 | A1 * | 9/2009 | Onoda et al. | 600/424 |
| 2009/0326556 | A1 | 12/2009 | Diolaiti et al. | |
| 2011/0178477 | A1 * | 7/2011 | Morel et al. | 604/264 |
| 2011/0202068 | A1 * | 8/2011 | Diolaiti et al. | 606/130 |
| 2012/0310254 | A1 * | 12/2012 | Manzo et al. | 606/130 |
| 2013/0066335 | A1 * | 3/2013 | Barwinkel et al. | 606/130 |
| 2013/0331858 | A1 * | 12/2013 | Devengenzo et al. | 606/130 |
| 2014/0039520 | A1 * | 2/2014 | Haider et al. | 606/130 |
| 2014/0296870 | A1 * | 10/2014 | Stern et al. | 606/130 |
| 2014/0316435 | A1 * | 10/2014 | Unsworth | 606/130 |

FOREIGN PATENT DOCUMENTS

| | | |
|---|---|---|
| KR | 10-2009-0076968 | 7/2009 |
| KR | 10-2011-0049703 | 5/2011 |
| WO | WO 03/077101 | 9/2003 |

OTHER PUBLICATIONS

JHU LCSR Robotics ("The da Vinci Robot Plays 'Operation' Board Game", YouTube, Apr. 5, 2011, http://youtu.be/rP25mga2x.*
European Search Report dated Apr. 5, 2013 from European Patent Application No. 12199530.

* cited by examiner

MEDICAL ROBOTIC SYSTEM INCLUDING SURGICAL INSTRUMENT POSITION DETECTION APPARATUS AND CONTROL METHOD THEREOF

CROSS-REFERENCE TO RELATED APPLICATIONS

This application claims the priority benefit of Korean Patent Application No. 10-2011-0145455, filed on Dec. 29, 2011, in the Korean Intellectual Property Office, the disclosure of which is incorporated herein by reference.

BACKGROUND

1. Field

Embodiments disclosed herein relate to a medical robot system that improves safety of robotic surgery and a control method thereof.

2. Description of the Related Art

Robotic surgery is a type of surgery that a medical professional (e.g., a surgeon or doctor) performs while controlling a robot to move a surgical instrument and is applied to various medical fields including surgery.

Generally, a medical robot system includes a robot including a robot arm and a console for an operator (e.g., a medical professional) to control the motion of the robot. An operator may directly move the robot arm having a surgical instrument or remotely control a motion of the robot arm through manipulation of an input unit provided in the console to incise or stitch a region for a surgical operation on a patient.

However, such a conventional medical robot system does not guarantee the safety of an incised region of the patient. Specifically, when the operator inserts the surgical instrument into the incised region of the patient and incises or stitches a region for surgery, the conventional medical robot system does not provide a location of the surgical instrument in the incised region.

For this reason, the operator does not know the location of the surgical instrument in the incised region while controlling a motion of the robot arm, and therefore, the incised region of the patient may be injured during surgery.

Also, the doctor may have difficulty controlling motion of the robot or the robot arm so as not to injure the incised region of the patient, and therefore, fatigue due to the use of the surgical robot may increase, which may result in an operator error during performance of the surgery.

SUMMARY

It is an aspect of the present invention to provide a medical robot system that detects position information of a surgical instrument in an incised region, thereby improving the safety of robotic surgery, and a control method thereof.

Additional aspects of the invention will be set forth in part in the description which follows and, in part, will be apparent from the description, or may be learned by practice of the invention.

In accordance with one aspect of the present invention, a medical robotic system includes a surgical instrument position detection apparatus to detect position information of a surgical instrument in a through-hole of a trocar inserted into an incised region of a patient when the surgical instrument is inserted into the through-hole and a console to control an operation of a surgical robot having the surgical instrument based on the detected position information of the surgical instrument.

The surgical instrument position detection apparatus may include a sensing unit including a first photodiode array mounted in a first subframe located in a horizontal direction on the basis of a predetermined vertex of a quadrangular frame and a second photodiode array mounted in a second subframe contacting the first subframe, a coordinate detection unit to detect an X-coordinate of the surgical instrument in the through-hole based on output values of the first photodiode array and a Y-coordinate of the surgical instrument in the through-hole based on output values of the second photodiode array, and a transmission unit to transmit the detected coordinate information to the console.

The coordinate detection unit may detect a position of a photodiode having a smallest output value among photodiodes of the first photodiode array as the X-coordinate of the surgical instrument and a position of a photodiode having a smallest output value among photodiodes of the second photodiode array as the Y-coordinate of the surgical instrument.

The medical robotic system may further include a coupler provided at one side of an open surface of the frame such that the coupler is coupled to the trocar, wherein the coupler may have a section of a shape corresponding to a section of the trocar.

The surgical instrument position detection apparatus may further include a light-emitting unit including a first light-emitting unit mounted in a third subframe facing the first subframe to emit light to the first photodiode array and a second light-emitting unit mounted in a fourth subframe facing the second subframe to emit light to the second photodiode array.

The console may generate a control signal to control the surgical robot according to a command input to the console when the detected position information of the surgical instrument is within a predetermined reference range.

The console may generate a control signal to control the surgical robot according to a predetermined surgical robot control mode when the detected position information of the surgical instrument is on a boundary of a predetermined reference range or out of the reference range.

The surgical robot control mode may be one selected from among a mode to stop motion of the surgical robot, a mode to move the surgical robot by a distance less than a distance based on a command input to the console, and a mode to reduce a moving speed of the surgical robot to a speed less than a speed based on a command input to the console.

In accordance with another aspect of the present invention, a control method of a medical robotic system includes detecting position information of a surgical instrument in a through-hole of a trocar inserted into an incised region of a patient when the surgical instrument is inserted into the through-hole and controlling an operation of a surgical robot having the surgical instrument based on the detected position information of the surgical instrument.

The detecting the position information of the surgical instrument may include detecting an X-coordinate and Y-coordinate of the surgical instrument in the through-hole based on output values of a first photodiode array mounted in a first subframe of a quadrangular frame located in a horizontal direction and output values of a second photodiode array mounted in a second subframe contacting the first subframe.

The detecting the X-coordinate and Y-coordinate of the surgical instrument may include detecting a position of a photodiode having a smallest output value among photodiodes of the first photodiode array as the X-coordinate of the surgical instrument and detecting a position of a photodiode having a smallest output value among photodiodes of the second photodiode array as the Y-coordinate of the surgical instrument.

The control method may further include emitting light to the first photodiode array using a first light-emitting unit mounted in a third subframe facing the first subframe and emitting light to the second photodiode array using a second light-emitting unit mounted in a fourth subframe facing the second subframe, which may be performed before the detecting the position information of the surgical instrument.

The controlling the operation of the surgical robot may include generating a control signal to control the surgical robot according to a command input to the console when the detected position information of the surgical instrument is within a predetermined reference range.

The controlling the operation of the surgical robot may include generating a control signal to control the surgical robot according to a predetermined surgical robot control mode when the detected position information of the surgical instrument is on a boundary of a predetermined reference range or out of the reference range.

The surgical robot control mode may be one selected from among a mode to stop motion of the surgical robot, a mode to move the surgical robot by a distance less than a distance based on a command input to the console, and a mode to reduce a moving speed of the surgical robot to a speed less than a speed based on a command input to the console.

In accordance with another aspect of the present invention, a control method of a robotic system includes receiving a position of an instrument inserted into a trocar disposed in a patient, and controlling an operation of a robot provided with the instrument, using the received position of the instrument. The controlling the operation of the robot may include comparing the received position of the instrument with a predetermined reference range corresponding to a circumferential region about the instrument, generating a control signal according to a result of the comparison, and transmitting the control signal to the robot to perform an operation using the instrument. A diameter of the predetermined reference range may be equal to or lesser than a diameter of a through-hole formed in the trocar.

When a user inputs a command to the robotic system, the generating the control signal may include generating a control signal according to the input command by maintaining the input command if the received position of the instrument is within the predetermined reference range, or generating a control signal according to the input command by modifying the input command if the received position of the instrument is on a boundary of the predetermined reference range or outside of the predetermined reference range. The input command may be modified by stopping a motion of the robot, moving the robot by a distance less than a distance input by the user, or reducing a moving speed of the robot to a speed less than a speed input by the user.

In accordance with another aspect of the present invention, a position detection apparatus may include a frame configured to be coupled to a trocar, the frame including a first subframe disposed in a first direction, and a second subframe disposed in a second direction, contacting the first subframe, a sensing unit, a light-emitting unit, a coordinate detection unit, and a transmission unit. The sensing unit comprising a first photodiode array may be mounted in the first subframe and a second photodiode array may be mounted in the second subframe. The light-emitting unit comprising a first light-emitting unit may be mounted in a third subframe facing the first subframe to emit light to the first photodiode array, and a second light-emitting unit may be mounted in a fourth subframe facing the second subframe to emit light to the second photodiode array. The coordinate detection unit may detect an X-coordinate of an instrument inserted into the trocar based on output values of the first photodiode array and a Y-coordinate of the instrument inserted into the trocar based on output values of the second photodiode array, and the transmission unit may transmit the detected coordinate information to the console. The frame may be a polygonal frame or the frame may be a circular frame, having a diameter equal to or greater than a diameter of the trocar.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Advantages and features of the present invention and a method of achieving the advantages and the features will be apparent by referring to embodiments described below in detail in connection with the accompanying drawings. However, the present invention is not limited to the embodiments disclosed below, but may be implemented in various forms. The embodiments disclosed here complete the disclosure of the present invention, and is provided to clearly inform those skilled in the art of the scope of the invention. The present invention is defined by the scope of the claims.

Reference will now be made in detail to the embodiments of the present invention, examples of which are illustrated in the accompanying drawings, wherein like reference numerals refer to like elements throughout.

Figure 1:
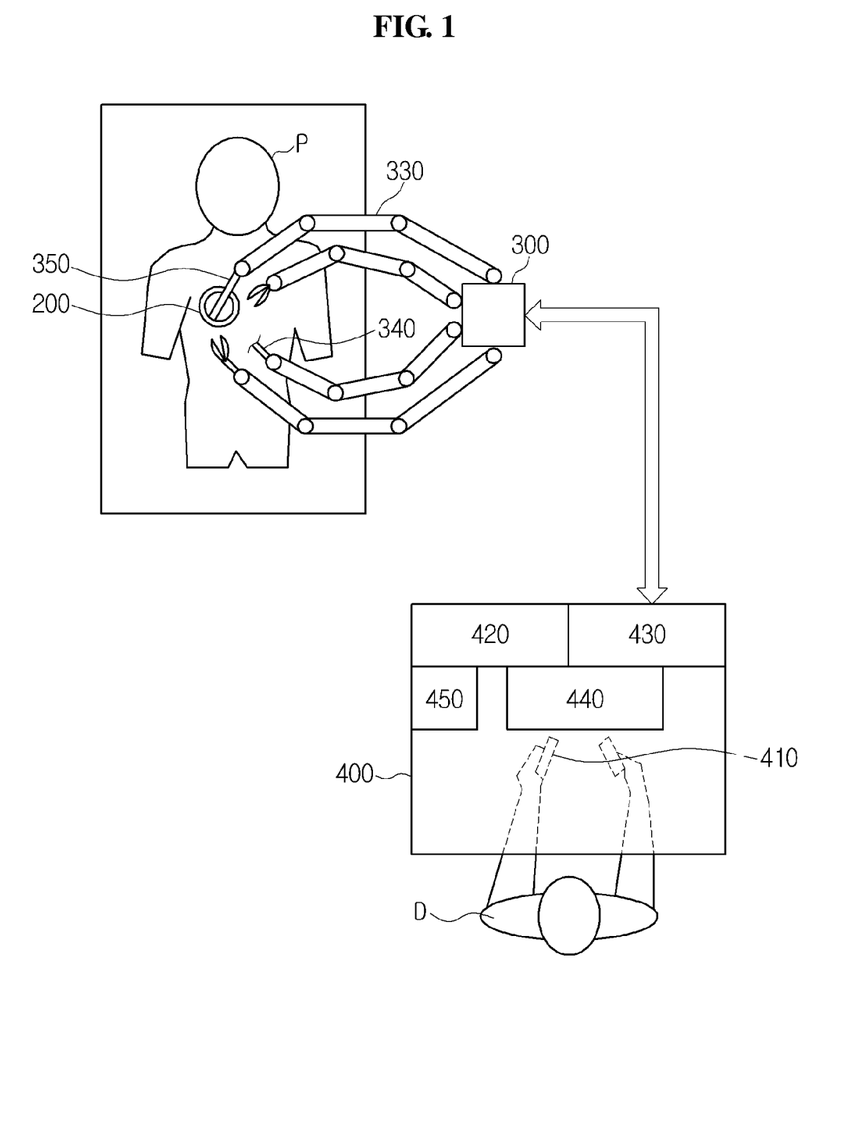
FIG. 1 is a view showing the construction of a medical robot system according to an embodiment of the present invention.

FIG. 1 is a view showing the construction of a medical robot system according to an embodiment of the present invention.

As shown in FIG. 1, the medical robot system may include a console 400, a surgical robot 300, and a trocar 200.

The console 400 may transmit a control signal to the surgical robot 300 or receive image data from the surgical robot 300. Also, the console 400 may receive position information of a surgical instrument 350 from a surgical instrument position detection apparatus 100 (see FIG. 2). To this end, the console 400 may be connected to the surgical robot 300 and/or the surgical instrument position detection apparatus 100 through a network. The network may be a wired network, a wireless network, or a combination thereof. The console 400 may display position information of the surgical instrument 350 as well as an image of a region for surgery in the body of a patient P. An operator (e.g., a medical professional such as a surgeon or doctor D) may remotely control the operation of the surgical robot 300 using the console 400. Hereinafter, for the sake of simplicity a doctor D is referred to as the operator. However, the operator need not necessarily be a doctor, although it would be expected that the operator is a qualified or authorized operator, e.g., a medical professional. However, broadly, the operator may be any user who controls the operation of the surgical robot 300. The console 400 will hereinafter be described in detail with reference to FIG. 6.

The surgical robot 300 may be a device which receives a control signal from the console 400 through the network and moves according to the received control signal. The surgical robot 300 may capture the region for surgery in the body of the patient P and transmit the captured image data to the console 400 through the network. The surgical robot 300 will hereinafter be described in detail with reference to FIG. 5.

The trocar 200 may be an instrument inserted into an incised region of the patient P. The trocar 200 serves to guide the surgical instrument 350 provided at the surgical robot 300. The trocar 200 may have a cylindrical body (not shown), and a through-hole (not shown). The surgical instrument 350 may be inserted through the through-hole, which may be formed in the center of the body. According to circumstances, one through-hole may be formed or several through-holes may be formed. In a case in which a plurality of through-holes are formed in the body of the trocar 200, a surgical instrument or a laparoscope may be inserted through one or more through-holes. The trocar 200 may be a tool inserted into the incised region of the patient P and thus may be made of an elastic material to minimize an injury to the incised region of the patient P. However, the material for the trocar 200 is not limited to such an elastic material.

According to an embodiment of the present invention, a surgical instrument position detection apparatus may be provided at the body of the trocar. When the surgical instrument 350 is inserted into the through-hole formed in the body of the trocar, the surgical instrument position detection apparatus may sense the position of the surgical instrument 350. The surgical instrument position detection apparatus will hereinafter be described in detail with reference to FIGS. 2 and 3.

Figure 2:
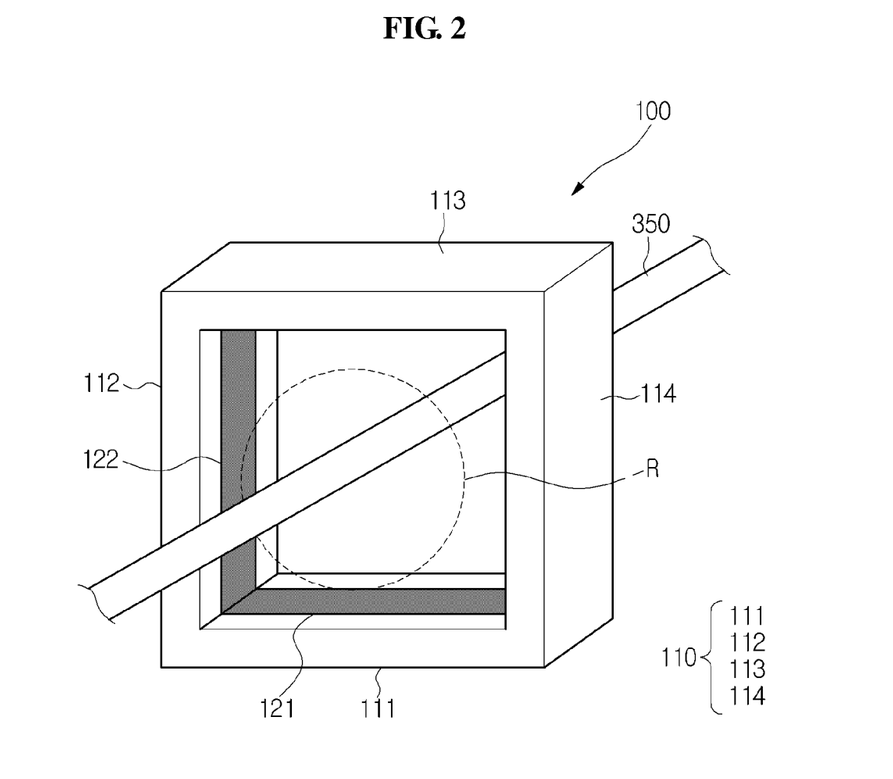
FIG. 2 is a view schematically showing the external appearance of a surgical instrument position detection apparatus according to an embodiment of the present invention.
Figure 3:
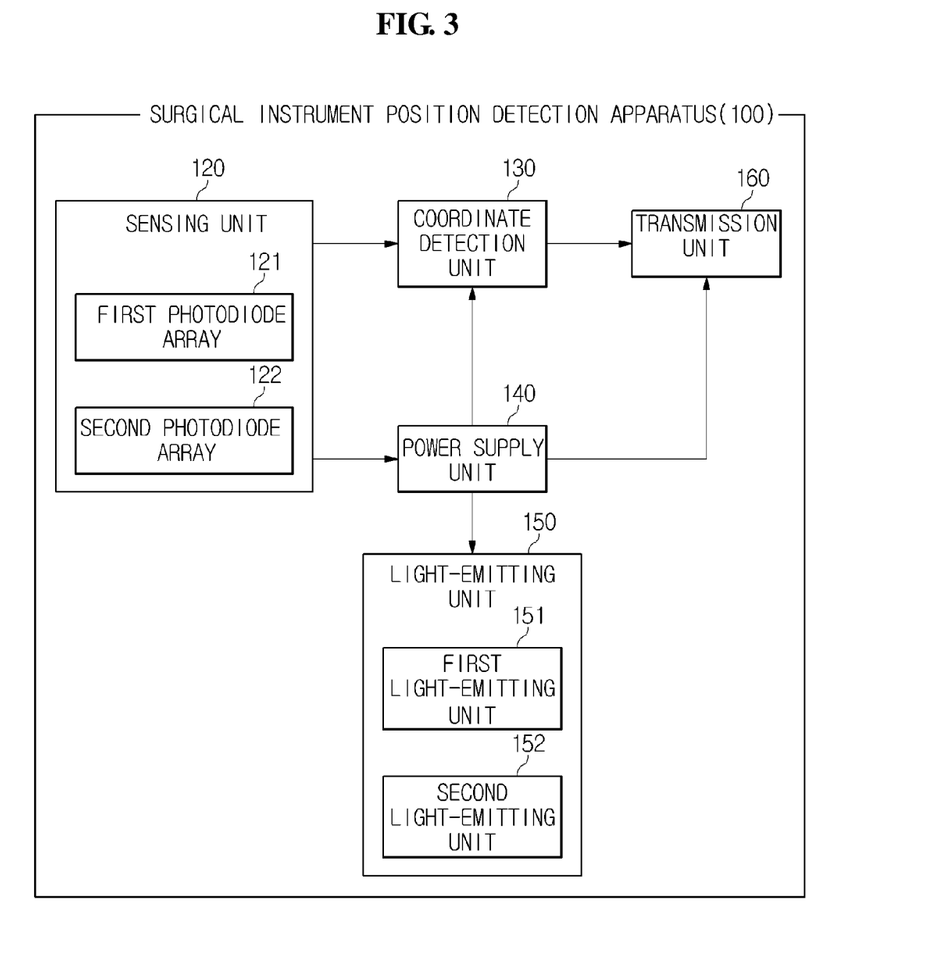
FIG. 3 is a view showing the control construction of the surgical instrument position detection apparatus according to the embodiment of the present invention.

FIG. 2 is a view schematically showing the external appearance of a surgical instrument position detection apparatus 100 according to an embodiment of the present invention, and FIG. 3 is a view showing the control construction of the surgical instrument position detection apparatus 100 according to the embodiment of the present invention.

As shown in FIG. 2, the external appearance of the surgical instrument position detection apparatus 100 may be realized by a quadrangular frame 110. FIG. 2 illustrates the quadrangular frame 110, but the present invention is not limited thereto. For example, the external appearance of the surgical instrument location position apparatus 100 may also be realized by a circular or polygonal frame. In a case in which the frame of the surgical instrument position detection apparatus 100 is circular, the size of the frame may be equal to or greater than the diameter of the body of the trocar. On the other hand, in a case in which the frame of the surgical instrument position detection apparatus 100 is polygonal, the size of the frame may be greater than the diameter of the body of the trocar 200.

The surgical instrument position detection apparatus 100 may be integrated with the trocar 200 or detachably coupled to the trocar 200. In a case in which the surgical instrument position detection apparatus 100 is realized by the quadrangular frame 110 as illustrated in FIG. 2, a coupler (not shown) may be provided at one side of an open surface of the frame such that the coupler is coupled to the trocar 200. The section of the coupler may have a shape corresponding to the section of the body of the trocar 200. For example, in a case in which the body of the trocar 200 is cylindrical, the coupler may also be cylindrical.

The coupler may be coupled to the trocar 200 in various ways. In an example, a spiral projection may be formed along the inner circumference of the coupler, and a spiral groove may be formed along the outer circumference of the body of the trocar 200 such that the lower part of the frame 110 and the upper part of the trocar 200 are coupled to each other by spiral coupling. In another example, two or more insertion grooves may be formed at predetermined positions of the outer circumference of the body of the trocar 200, and two or more projections may be formed at the inner circumference of the coupler. The projections formed on the inner circumference of the coupler may be inserted into the insertion grooves formed on the outer circumference of the body of the trocar such that the frame 110 and the trocar are coupled to each other.

As shown in FIG. 3, the surgical instrument position detection apparatus 100 may include a sensing unit 120, a light-emitting unit 150, a coordinate detection unit 130, a transmission unit 160, and a power supply unit 140. These components may be provided in the quadrangular frame 110 as illustrated in FIG. 2.

When the surgical instrument 350 is inserted into the through-hole formed on the body of the trocar 200, the sensing unit 120 may sense the surgical instrument 350. To this end, the sensing unit 120 may include a photodiode array. The photodiode array may refer to an array in which a plurality of photodiodes are arranged at regular intervals of a few mm or μm. The photodiode may be a device which converts light energy into electric energy. When light contacts the photodiode, current flows in the photodiode. The amplitude of voltage output from the photodiode is almost proportional to the intensity of the light. For example, as the intensity of the light increases, the amplitude of voltage output from the photodiode may increase. A plurality of photodiodes may be arranged, for example, in a line to form a photodiode array. The plurality of photodiodes may be arranged in other patterns however to form the photodiode array, and is not limited to a line.

As shown in FIG. 2, photodiode arrays may be mounted in two subframes perpendicular to each other among four subframes 111, 112, 113, and 114 forming the quadrangular frame 110. Specifically, assuming that a vertex located at the bottom left side of the quadrangular frame 110 is the origin, the photodiode arrays may be mounted in the subframe 111 located in the horizontal direction on the basis of the origin and the subframe 112 located in the vertical direction on the basis of the origin. In the following description, the photodiode array mounted in the subframe 111 located in the horizontal direction will be referred to as a 'first photodiode array 121'. Also, the photodiode array mounted in the subframe 112 located in the vertical direction will be referred to as a 'second photodiode array 122'. Alternatively, a first photodiode array may be disposed in subframe 113, and a second photodiode array may be disposed in subframe 114, which may be perpendicular to subframe 113. Other arrangements are possible including a first photodiode array disposed in subframe 113, and a second photodiode array disposed in subframe 112, or a first photodiode array disposed in subframe 111, and a second photodiode array may be disposed in subframe 114. Further, photodiode arrays may be disposed in all of the subframes 111 through 114.

The light-emitting unit 150 emits light when voltage is applied thereto. For example, the light-emitting unit 150 may be realized by one or more light-emitting diodes. The light-emitting unit 150 may include a first light-emitting unit 151 and a second light-emitting unit 152. The first light-emitting unit 151 may be mounted at a side of the quadrangular frame 110 which is opposite to the first photodiode array 121 to emit light to the first photodiode array 121. Also, the second light-emitting unit 152 may be mounted at a side of the quadrangular frame 110 which is opposite to the second photodiode array 122 to emit light to the second photodiode array 122. That is, the first and second light-emitting units may be disposed on sides of the quadrangular frame 110 which are opposite to those sides or sub-frames on which photodiode arrays are disposed. In the event photodiode arrays are disposed on each of the sub-frames, additional light-emitting units may be used and disposed on each side of the frame. In this case, the surgical instrument position detection apparatus 100 may selectively select two of the four light-emitting units to generate and emit light to respective photodiode arrays which are opposite to the selected light-emitting units. Additional light emitting units and photodiode arrays may provide for an additional layer of redundancy.

The coordinate detection unit 130 may detect the position, e.g., an X-coordinate and Y-coordinate, of the surgical instrument 350, based on output values of the first photodiode array 121 and output values of the second photodiode array 122. Specifically, in the quadrangular frame 110, the subframe 111 located in the horizontal direction may be considered as an X-axis of an XY coordinate system, and the subframe 112 located in the vertical direction may be considered as a Y-axis of the XY coordinate system. Consequently, the coordinate detection unit 130 may detect the X-coordinate of the surgical instrument 350 based on the output values of the first photodiode array 121 and the Y-coordinate of the surgical instrument 350 based on the output values of the second photodiode array 122. The coordinate detection unit 130 may detect the position of the photodiode having the smallest output value among the photodiodes included in the first photodiode array 121 as the X-coordinate of the surgical instrument 350. In the same manner, the coordinate detection unit 130 may detect the position of the photodiode having the smallest output value among the photodiodes included in the second photodiode array 122 as the Y-coordinate of the surgical instrument 350. A more detailed description thereof will be given with reference to FIG. 4. As mentioned above, the vertex formed by sub-frame 111 and sub-frame 112 may be considered as an origin for the XY coordinate system. Alternatively, another vertex may be used as an origin for the XY coordinate system, and X-axis and Y-axis arrangements may be reversed, if desired.

In an alternative embodiment in which the external appearance of the surgical instrument position detection apparatus 100 is realized by a circular frame, the frame may be segmented symmetrically, for example, into two or more subframes which form the circular frame. Photodiodes may be disposed in portions of one or more subframes while light emitting units may be disposed on portions of one or more subframes which are opposite of the portions having the photodiodes.

Figure 4:
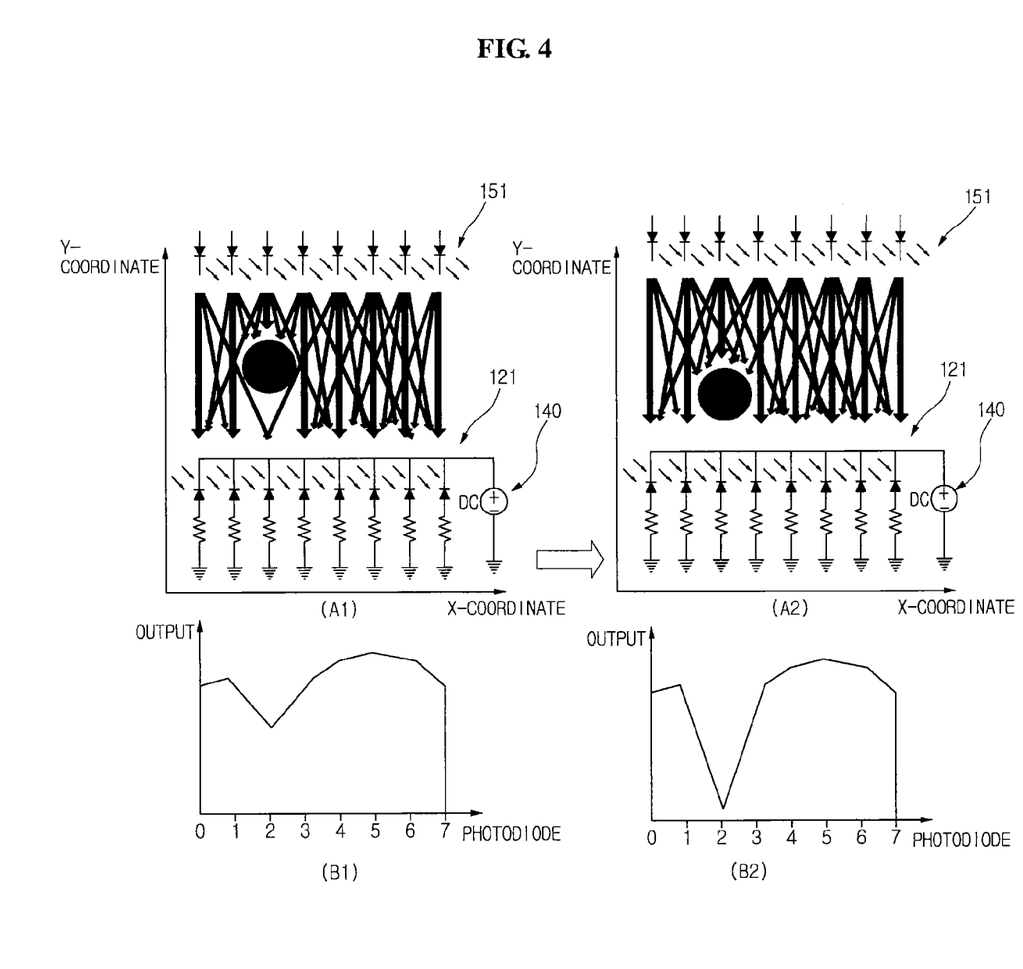
FIG. 4 is a view illustrating a method of detecting coordinates of a surgical instrument.

FIG. 4 is a view illustrating a method of detecting coordinates of the surgical instrument 350.

FIG. 4(A1) is a view showing that the surgical instrument 350 is disposed between the first light-emitting unit 151 and the first photodiode array 121, and FIG. 4(B1) is a graph showing output values of the first photodiode array 121 at a corresponding time. FIG. 4(A2) is a view showing that only the position of the Y-axis of the surgical instrument 350 has been changed from FIG. 4(A1), and FIG. 4(B2) is a graph showing output values of the first photodiode array 121 at a corresponding time. In FIG. 4(A1) and FIG. 4(A2), the thickness of the arrow indicates the intensity of light. As stated above, the coordinate detection unit 130 may detect the X-coordinate of the surgical instrument 350 based on the output values of the first photodiode array 121, where the photodiode having the smallest output value among the photodiodes included in the first photodiode array 121 may correspond to the X-coordinate of the surgical instrument 350. As can be seen from FIG. 4, photodiode 2 has an output value lower than the remaining photodiodes in the photodiode array. Therefore, the coordinate detection unit 130 may detect the position of the second photodiode of the first photodiode array 121 as the X-coordinate of the surgical instrument 350.

Referring to FIG. 4(A1) and FIG. 4(A2), when the surgical instrument 350 is disposed between the first light-emitting unit 151 and the first photodiode array 121, the amounts of light received by respective photodiodes of the first photodiode array 121 are different. This is because light emitted from light-emitting diodes disposed differently from the surgical instrument among the light-emitting diodes of the first light-emitting unit 151 affects the photodiodes corresponding to the position of the surgical instrument 350. Such a phenomenon occurs because light scatters in the air.

Referring to FIG. 4(B1) and FIG. 4(B2), when only the Y-coordinate is changed in a state in which the X-coordinate of the surgical instrument 350 is fixed, an output value of each photodiode of the first photodiode array 121 becomes different from the previous value, but an output value of the photodiode corresponding to the position of the surgical instrument 350 is kept minimum. Consequently, a photodiode having the smallest output value among the photodiodes included in the first photodiode array 121 may be detected, and the position of the detected photodiode may be determined as the X-coordinate of the surgical instrument 350. The Y-coordinate of the surgical instrument 350 may be detected in the same manner as the X-coordinate of the surgical instrument 350.

Referring back to FIG. 3, the transmission unit 160 may transmit the detected position information of the surgical instrument 350 to the console 400. To this end, the transmission unit 160 may perform wired or wireless communication with the console 400, or a combination thereof.

The power supply unit 140 may supply power to the components in the surgical instrument position detection apparatus 100. If voltages to operate the respective components of the surgical instrument position detection apparatus 100 are different, the power supply unit 140 may include a plurality of power supply units (not shown) to supply different voltages.

Figure 5:
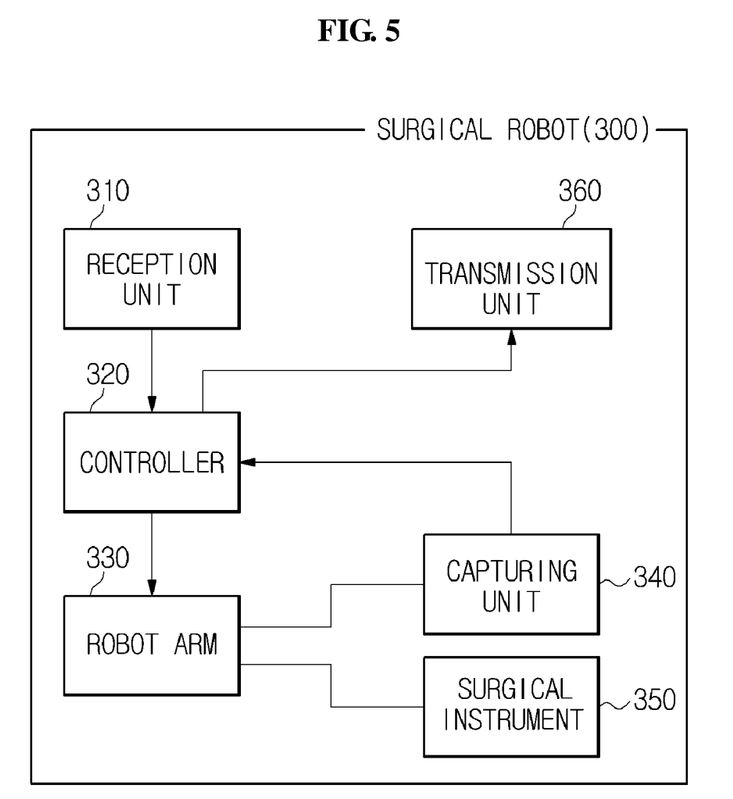
FIG. 5 is a view showing the construction of a surgical robot according to an embodiment of the present invention.

FIG. 5 is a view showing the construction of a surgical robot 300 according to an embodiment of the present invention.

As shown in FIG. 5, the surgical robot 300 may include a reception unit 310, a transmission unit 360, a controller 320, a robot arm 300, a capturing unit 340 and a surgical instrument 350. Here, it is noted that the robot arm 300 and surgical instrument 350 may be positioned in a surgery site as needed to perform the desired operation. For example, the robot arm and surgical instrument may be portable, may be fixed, or may be detachably disposed to a site (e.g., the railing of an operating table, or other object).

The reception unit 310 may receive a control signal from the console 400. The received control signal may be provided to the controller 320, which will hereinafter be described. The reception unit 310 may receive the control signal from the console 400 over a wired or wireless network, or a combination thereof.

The controller 320 may control motion of the robot arm 330 according to the control signal received by the reception unit 310.

The robot arm 330 may be controlled by the controller 320. The capturing unit 340 and the surgical instrument 350 may be provided at one end of the robot arm 330. As shown in FIG. 1, there may be a plurality of robot arms provided at the surgical robot 300.

The capturing unit 340 may capture a region for surgery in the body of the patient P. An image captured by the capturing unit 340 may be provided to the controller 340, where the image passes through a predetermined image-processing process. Some examples of image processing may include extension, reduction, rotation, editing, and filtering of the captured image. Some or all of the image processing processes performed by the controller 320 may be omitted as needed, or may be performed separately by another image processing unit remotely located from the surgical robot 300. For example, image processing may be performed by an image processing unit (not shown) included the at the console 400.

The surgical instrument 350 may be provided at one end of the robot arm 350. The surgical instrument 350 may be detachable from the robot arm 330. The doctor D may manipulate an input unit 410 provided in the console 400 to incise or stitch a region for surgery in the body of the patient P while moving the surgical instrument 350.

The transmission unit 360 may transmit image data captured by the capturing unit 340 or image data, image processing of which has been completed by the controller 320, to the console 400. The transmission unit 310 may transmit the image data to the console 400 over a wired or wireless network, or a combination thereof.

Figure 6:
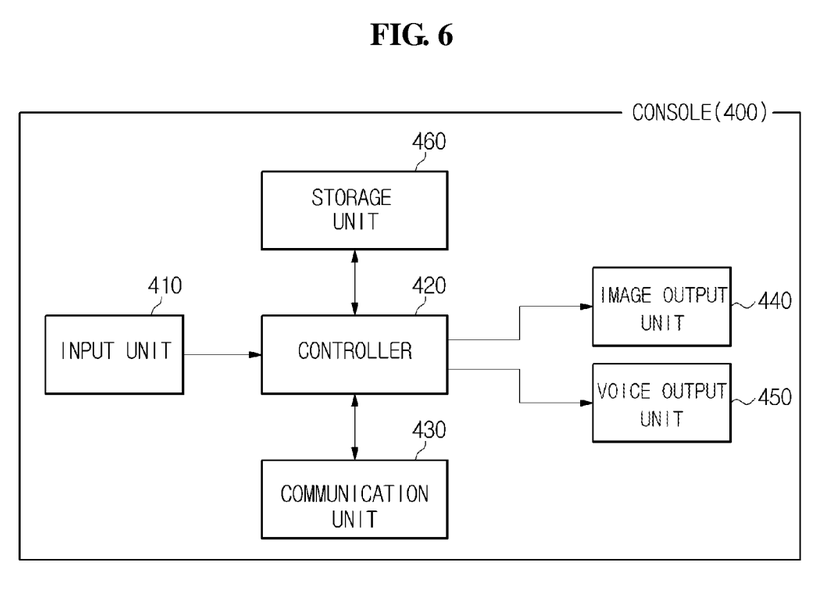
FIG. 6 is a view showing the construction of a console according to an embodiment of the present invention.

FIG. 6 is a view showing the construction of a console 400 according to an embodiment of the present invention.

As shown in FIG. 6, the console 400 may include an input unit 410, a storage unit 460, a controller 420, a communication unit 430, an image output unit 440, and a voice output unit 450.

The input unit 410 may receive a command to control motion of the surgical robot 300 from the doctor D. Also, the input unit 410 may receive information regarding a reference range R (see FIG. 2) from the doctor D. The reference range R may refer to a range within which an incised region of the patient P is not injured even if the surgical instrument 350 moves in a state in which the surgical instrument 350 is inserted in the through-hole of the trocar 200. As can be seen from FIG. 2, the reference range R may correspond to a circumferential region about the longitudinal axis of the surgical instrument 350, in which the surgical instrument 350 may safely be moved without risk (or within an acceptable risk) of injury to the patient.

The reference range R may be set based on the section of the through-hole formed in the trocar 200. Even if the surgical instrument position detection apparatus 100 is realized by the quadrangular frame 110, the section of the through-hole formed in the trocar 200 is generally circular. If the frame of the surgical instrument position detection apparatus 100 is realized by the quadrangular frame 110, the trocar 200 may be positioned within the quadrangular frame 110. In this case, the reference range R may be set based on the section of the through-hole formed in the trocar 200. The reference range R may be set to be equal to the diameter of the through-hole formed in the trocar 200 or to be less than the diameter of the through-hole. If the frame of the surgical instrument position detection apparatus 100 is circular, the size of the frame may be equal to or greater than the diameter of the body of the trocar. The through-hole may be formed in the trocar 200. Thus, the reference range R may be set to be equal to the diameter of the through-hole formed in the trocar 200 or to be less than the diameter of the through-hole.

Also, the diameter of the trocar 200 to be used with respect to the patient P may be different according to the type of surgery. The doctor D may preset the reference range R based on the diameter of the trocar 200 to be used in the surgery. A method of setting the reference range R may include a method of the doctor D directly inputting a value of the reference range R or a method of selecting one of the set values of the reference range R stored in the console 400. The set value of the reference range R may be a value basically stored in the production process of the console 400, a value previously input by the doctor D, or a combination thereof. For example, values of the reference range R may be stored in a table in which a value corresponds to a type of surgery, or the value may correspond to a size of trocar used in the surgery. The table may be stored in storage unit 460, which is discussed later.

In addition, the doctor D may set whether to display position information of the surgical instrument 350, surgical robot control modes in the case of an emergency, whether to output an alarm in an emergency, and alarm output modes through the input unit 410. To this end, the input unit 410 may include a plurality of buttons, keys, and joysticks. Also, the input unit 410 may include an apparatus or device such as keyboard, pedal or footswitch, or mouse to enable an operator to control the surgical robot. The input unit 410 may further have additional features to assist the user in operating the surgical robot, including haptic feedback capability, head-mounted displays, or virtual reality devices, for example.

The communication unit 430 may perform transmission and reception of data or a control signal between the console 400 and the surgical robot 300. Specifically, the communication unit 430 may transmit a control signal to control the operation of the surgical robot 300 to the surgical robot 300. The communication unit 430 may perform transmission and reception of data or a control signal between the console 400 and the surgical robot 300, over a wired or wireless network, or a combination thereof.

The communication unit 430 may receive image data captured by the capturing unit 340 of the surgical robot 300 or image data, image processing of which has been completed by the controller of the surgical robot 300. Also, the communication unit 430 may receive position information of the surgical instrument 350 from the surgical instrument position detection apparatus 100. The received position information of the surgical instrument 350 may be provided to the controller 420. Alternatively, images captured by capturing unit 340 may be directly transmitted to the console 400 via the communication unit 430. The controller 420 may perform image processing similar to that performed by controller 320 of the surgical robot 300, to obtain image data.

The controller 420 may generate a control signal to control the surgical robot 300 according to a command input through the input unit 410. The control signal generated by the controller 420 may be transmitted to the surgical robot 300 via the communication unit 430.

Also, the controller 420 may compare the position information of the surgical instrument 350 received from the surgical instrument position detection apparatus 100 with the reference range R. The controller 420 may generate a control signal to control the surgical robot 300 according to a result of the comparison.

For example, upon determining that the position information of the surgical instrument 350 is within the reference range R, the controller 420 generates a control signal to control the surgical robot 300 according to a command input by the doctor D.

Also, upon determining that the position information of the surgical instrument 350 is on the boundary of the reference range or out of the reference range, the controller 420 may determine that an emergency situation has occurred and generate a control signal to control the surgical robot 300 according to a predetermined surgical robot control mode.

In an example, if the predetermined surgical robot control mode is to stop motion of the surgical robot, the controller 420 may generate a control signal to stop the motion of the surgical robot.

In another example, if the predetermined surgical robot control mode is to reduce the moving distance of the surgical robot, the controller 420 may generate a control signal to move the surgical robot 300 by a distance less than a distance based on the command input by the doctor D. That is, if the command input by the doctor D is a command to move the surgical robot 300 by 5 mm, the controller 420 may generate a control signal to move the surgical robot 300 by 1 mm. For example, the controller 420 may generate a control signal to move the surgical robot a distance which is a proportional or fractional amount of the command input (e.g., moving the surgical robot a distance which is ½, ⅓, ¼, ⅕, etc. of the amount input by the doctor D).

In a further example, if the predetermined surgical robot control mode is to reduce a moving speed of the surgical robot, the controller 420 may generate a control signal to reduce the moving speed of the surgical robot 300 to less than the speed at which the doctor D has manipulated the input unit 410. For example, if the doctor D has manipulated the input unit 410 at a high speed, the controller 420 may generate a control signal to move the surgical robot 300 at a speed less than the speed at which the doctor D has manipulated the input unit 410. For example, the controller 420 may generate a control signal to move the surgical robot a speed which is a proportional or fractional amount of the command input (e.g., moving the surgical robot at a speed which is ½, ⅓, ¼, ⅕, etc. of the amount input by the doctor D).

The storage unit 460 may store an algorithm to control the operation of the surgical robot 300, data received from the surgical robot 300, data received from the surgical instrument position detection apparatus 100, and data to determine emergency, such as information regarding the reference range R.

Also, the storage unit 460 may store information set by the user. Some examples of the set information may include whether to display position information of the surgical instrument 350, surgical robot control modes in an emergency, whether to output an alarm in an emergency, and alarm output modes. Some examples of the alarm output modes may include an alarm sound, an alarm light, display of a warning message, a vibration sent to the user via the joystick or input unit, and flickering of an icon.

The storage unit 460 may be realized by a non-volatile memory device such as a read only memory (ROM), a random access memory (RAM), a programmable read only memory (PROM), an erasable programmable read only memory (EPROM), or a flash memory, a volatile memory device such as a random access memory (RAM), or a storage medium such as a hard disk or optical disk. However, the present invention is not limited thereto. The storage unit 460 may be realized in any other form well-known in the art to which the present invention pertains.

The communication unit 430 may perform transmission and reception of data or a control signal between the console 400 and the surgical robot 300. Specifically, the communication unit 430 may transmit a control signal to control the operation of the surgical robot 300 to the surgical robot 300 and receive image data captured by the capturing unit 340 of the surgical robot 300.

Also, the communication unit 430 may receive position information of the surgical instrument 350 from the transmission unit 160 of the surgical instrument position detection apparatus 100. The position information may be coordinate information of the surgical instrument 350 which may be positioned in the through-hole. The received position information may be provided to the controller 420.

The controller 420 may generate a control signal to control the surgical robot 300 according to a command input through the input unit 410. The control signal generated by the controller 420 may be transmitted to the surgical robot 300 via the communication unit 430. The control signal generated by the controller 420 may be dependent upon the position information received by the communication unit 430. That is the controller may analyze the position information to selectively determine whether the command input by a user through the input unit 410 needs to be adjusted or modified, stopped, or allowed unchanged or maintained.

The image output unit 440 may display an image captured by the surgical robot 300. Also, the image output unit 440 may overlap the position information of the surgical instrument 350 with the image captured by the surgical robot 300 and display the overlapped information. The image output unit 440 may be realized by, for example, a liquid crystal display (LCD). However, displays other than a LCD display may be utilized, including a LED display for example.

The voice output unit 450 may output an alarm related to an occurrence of an emergency situation as a sound. The voice output unit 450 may include, for example, a speaker.

Figure 7:
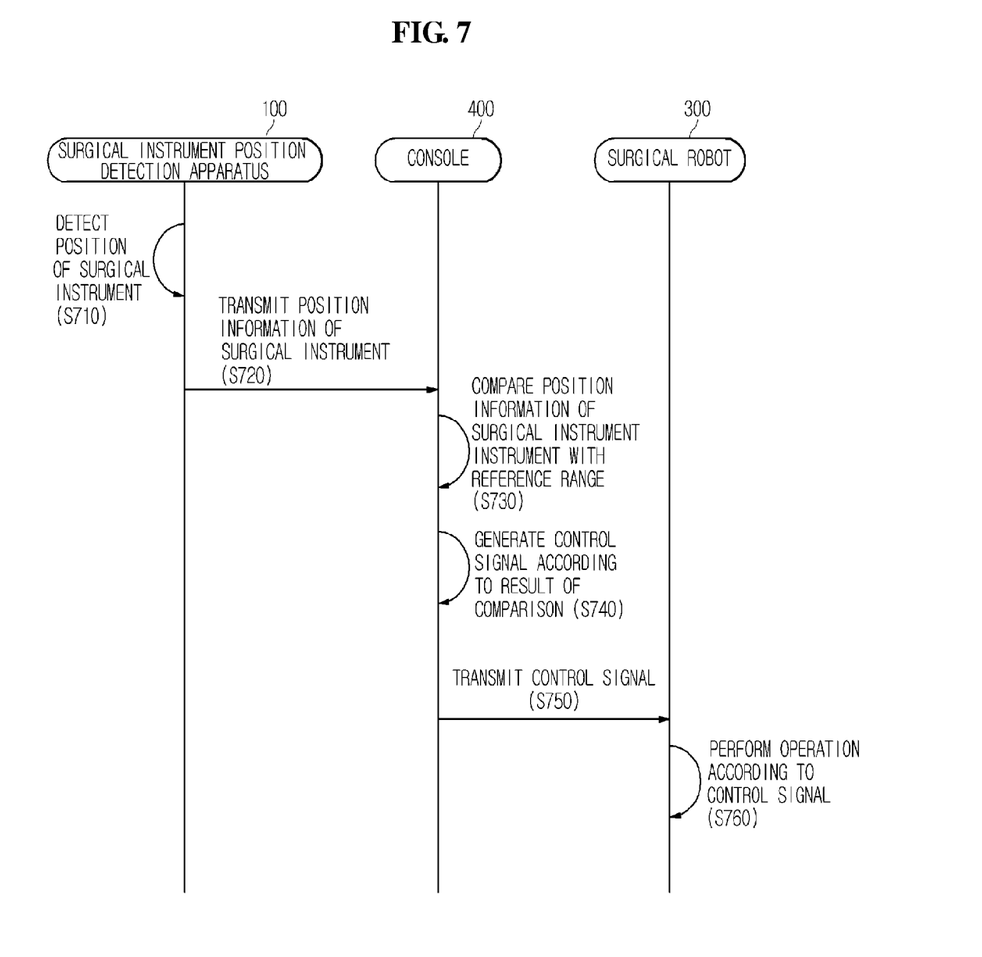
FIG. 7 is a flowchart showing a process of controlling a medical robot system according to an embodiment of the present invention.

FIG. 7 is a flowchart showing a process of controlling a medical robot system according to an embodiment of the present invention.

First, it is assumed that the trocar 200, to which the surgical instrument position detection apparatus 100 is coupled, is inserted in an incised region of the patient P. Also, it is assumed that the reference range R for the position of the surgical instrument 350 has already been input or set in the console 400.

When the surgical instrument 350 is inserted into the through-hole of the trocar 200 in this state, the surgical instrument position detection apparatus 100 may detect the position of the surgical instrument 350 in the through-hole (S710). Operation S710 of detecting the position of the surgical instrument 350 may include the first light-emitting unit 151 and the second light-emitting unit 152 emitting light to the first photodiode array 121 and the second photodiode array 122, respectively, detecting a photodiode having the smallest output value among the photodiodes included in the first photodiode array 121, detecting a photodiode having the smallest output value among the photodiodes included in the second photodiode array 122, and determining the positions of the detected photodiodes as an X-coordinate and Y-coordinate of the surgical instrument 350.

When the position of the surgical instrument 350 is detected, the surgical instrument position detection apparatus 100 may transmit the detected position information of the surgical instrument 350 to the console 400 via a network (S720).

The console 400 may receive the position information of the surgical instrument 350 from the surgical instrument position detection apparatus 100 and compare the received position information of the surgical instrument 350 with the reference range R (S730).

The console 400 may generate a control signal to control the surgical robot 300 according to a result of the comparison (S740). Operation of generating a control signal according to a result of the comparison may include generating a control signal according to a command input by the doctor D when the position of the surgical instrument 350 is within the reference range R and generating a control signal according to a predetermined surgical robot control mode when the position of the surgical instrument 350 is on or near the boundary of the reference range R or out of the reference range R.

Operation of generating a control signal according to a predetermined surgical robot control scheme may include at least one selected from among stopping motion of a surgical robot, generating a control signal to move the surgical robot 300 by a distance less than a desired distance set according to the command input by the doctor D, and generating a control signal to reduce the moving speed of the surgical robot 300 to less than the speed at which the doctor D has manipulated the input unit 410.

The control signal generated by the console 400 may be transmitted to the surgical robot 300 (S750). Consequently, the surgical robot 300 may operate according to the received control signal (S760).

In FIG. 7, the position information of the surgical instrument 350 is compared with the reference range R. Determining that the position of the surgical instrument 350 is on or near the boundary of the reference range R or out of the reference range R, the console 400 may generate an alarm. Operation of generating an alarm may be performed between operations S730 and S740 or between operations S740 and S750.

In the above embodiments, the components constituting the surgical instrument position detection apparatus 100, the surgical robot 300, and the console 400 may be realized by a kind of module. The module may include software components or hardware components, such as a field programmable gate array (FPGA) or an application specific integrated circuit (ASIC), to perform a specific function. However, the module is not limited to software or hardware. The module may be configured to be present in an addressable storage medium or to execute one or more processors.

For example, the module may include components, such as software components, object-oriented software components, class components, and task components, processes, functions, attributes, procedures, subroutines, segments of a program code, drivers, firmware, microcode, circuitry, data, databases, data structures, tables, arrays, and variables. Functions provided by the components and modules may be combined into fewer components and modules or further divided into additional components and modules. In addition, the components and modules may execute one or more central processing units (CPUs) in a device.

The components constituting the surgical instrument position detection apparatus 100, the surgical robot 300, and the console 400 and corresponding methods for controlling the components according to the above-described example embodiments may use one or more processors, which may include a microprocessor, central processing unit (CPU), digital signal processor (DSP), or application-specific integrated circuit (ASIC), as well as portions or combinations of these and other processing devices.

In addition to the above embodiments, embodiments of the present invention may also be realized by a medium including a computer readable code/command to control at least one processing element of the above embodiments, e.g. a computer readable medium. The medium may correspond to any medium/media enabling the storage and/or transmission of the computer readable code.

The computer readable code may be recorded in a medium or transmitted through the Internet. The medium may include a recording medium, such as a magnetic storage medium (for example, a ROM, a floppy disk, or a hard disk) or an optical medium (for example, a compact disk read only memory (CD-ROM) or a digital versatile disk (DVD)), or a transmission medium, such as a carrier wave. Also, according to embodiments of the present invention, the medium may be a signal, such as a composite signal or a bitstream. The medium may also be a distributed network, and therefore, the computer readable code may be stored/transmitted and executed in a distributed fashion. In addition, for example, a processing element may include a processor or a computer processor. The processing element may be distributed and/or included in a device.

Each block of the flowchart illustrations may represent a unit, module, segment, or portion of code, which comprises one or more executable instructions for implementing the specified logical function(s). It should also be noted that in some alternative implementations, the functions noted in the blocks may occur out of the order. For example, two blocks shown in succession may in fact be executed substantially concurrently or the blocks may sometimes be executed in the reverse order, depending upon the functionality involved.

As is apparent from the above description, a medical robot system and a control method thereof according to embodiments of the present invention have the following effects.

Position information of a surgical instrument in an incised region of a patient is detected, and a surgical robot is controlled according to the detected position information of the surgical instrument, thereby preventing the incised region of the patient from being injured by the surgical instrument.

The surgical robot is controlled such that the surgical instrument moves only within a predetermined range of the incised region of the patient based on the position information of the surgical instrument, thereby improving safety of robotic surgery.

The disclosure herein has provided example embodiments of a medical robotic system including the surgical instrument position detection apparatus 100, the surgical robot 300, and the console 400 and control methods thereof, which may be applied for example, in a medical setting to perform an operation on a patient (e.g., a human or animal or other lifeform). However, the disclosure is not so limited. For example, the medical robotic system may be used in other settings which may benefit from the example embodiments disclosed herein. For example, the surgical robot may be utilized to perform operations in any confined space or enclosure in which an operator may need to perform controlled movements using an instrument attached to a robot arm, so as to avoid or to prevent injuries to bodies or objects, that may be located or disposed within the space or enclosure, due to imprecise movements of the surgical robot. Possible settings may include, for example, mining operations, surveillance operations, inspection operations, repair operations, bomb disposal operations, etc., however again, the disclosure is not so limited.

Although a few example embodiments of the present invention have been shown and described, it would be appreciated by those skilled in the art that changes may be made to these embodiments without departing from the principles and spirit of the invention, the scope of which is defined in the claims and their equivalents.

What is claimed is:

1. A medical robotic system comprising:
a surgical instrument position detection apparatus configured to detect position information of a surgical instrument inserted in a trocar which is inserted into an incised region of a patient; and
a console configured to control an operation of a surgical robot having the surgical instrument, based on the detected position information of the surgical instrument,
wherein the surgical instrument position detection apparatus comprises
a quadrangular frame forming an external appearance of the surgical instrument position detection apparatus including a first subframe disposed in a horizontal direction, and a second subframe disposed in a vertical direction, contacting the first subframe;
a sensing unit comprising a first photodiode array mounted in the first subframe and a second photodiode array mounted in the second subframe;
a coordinate detection unit to detect an X-coordinate of the surgical instrument in the trocar based on output values of the first photodiode array and a Y-coordinate of the surgical instrument in the trocar based on output values of the second photodiode array.

2. The medical robotic system according to claim 1, wherein the surgical instrument position detection apparatus further comprises:
a transmission unit to transmit the detected coordinate information to the console.

3. The medical robotic system according to claim 1, wherein the coordinate detection unit detects:
a position of a photodiode having a smallest output value among photodiodes of the first photodiode array as the X-coordinate of the surgical instrument; and
a position of a photodiode having a smallest output value among photodiodes of the second photodiode array as the Y-coordinate of the surgical instrument.

4. The medical robotic system according to claim 1, further comprising:
a coupler provided at one side of an open surface of the frame such that the coupler is coupled to the trocar, wherein
the coupler has a section of a shape corresponding to a section of the trocar.

5. The medical robotic system according to claim 1, wherein
the surgical instrument position detection apparatus further comprises a light-emitting unit comprising:
a first light-emitting unit mounted in a third subframe facing the first subframe to emit light to the first photodiode array; and
a second light-emitting unit mounted in a fourth subframe facing the second subframe to emit light to the second photodiode array.

6. The medical robotic system according to claim 1, wherein the console generates a control signal to control the surgical robot according to a command input to the console when the detected position information of the surgical instrument is within a predetermined reference range.

7. The medical robotic system according to claim 1, wherein the console generates a control signal to control the surgical robot according to a predetermined surgical robot control mode when the detected position information of the surgical instrument is on a boundary of a predetermined reference range or out of the reference range.

8. The medical robotic system according to claim 7, wherein the predetermined surgical robot control mode is one selected from among a mode to stop motion of the surgical robot, a mode to move the surgical robot by a distance less than a distance input to the console, and a mode to reduce a moving speed of the surgical robot to a speed less than a speed input to the console.

9. A control method of a medical robotic system comprising:
detecting position information of a surgical instrument inserted in a trocar which is inserted into an incised region of a patient; and
controlling an operation of a surgical robot having the surgical instrument based on the detected position information of the surgical instrument,
wherein a quadrangular frame surrounds the trocar and includes a first subframe disposed in a horizontal direction, and a second subframe disposed in a vertical direction, contacting the first subframe, and
the detecting the position information of the surgical instrument comprises detecting an X-coordinate and Y-coordinate of the surgical instrument in the trocar based on output values of a first photodiode array mounted in the first subframe and output values of a second photodiode array mounted in the second subframe.

10. The control method according to claim 9, wherein the detecting the X-coordinate and Y-coordinate of the surgical instrument comprises:
detecting a position of a photodiode having a smallest output value among photodiodes of the first photodiode array as the X-coordinate of the surgical instrument; and
detecting a position of a photodiode having a smallest output value among photodiodes of the second photodiode array as the Y-coordinate of the surgical instrument.

11. The control method according to claim 9, further comprising: emitting light to the first photodiode array using a first light-emitting unit mounted in a third subframe facing the first subframe; and
emitting light to the second photodiode array using a second light-emitting unit mounted in a fourth subframe facing the second subframe.

12. The control method according to claim 9, wherein the controlling the operation of the surgical robot comprises generating a control signal to control the surgical robot according to a command input to a console when the detected position information of the surgical instrument is within a predetermined reference range.

13. The control method according to claim 9, wherein the controlling the operation of the surgical robot comprises generating a control signal to control the surgical robot according to a predetermined surgical robot control mode when the detected position information of the surgical instrument is on a boundary of a predetermined reference range or out of the reference range.

14. The control method according to claim 13, wherein the predetermined surgical robot control mode is one selected from among a mode to stop motion of the surgical robot, a mode to move the surgical robot by a distance less than a distance input to a console, and a mode to reduce a moving speed of the surgical robot to a speed less than a speed input to the console.

15. A control method of a robotic system comprising:
detecting a position of an instrument inserted into a trocar disposed in a patient; and
controlling an operation of a robot provided with the instrument, using the detected position of the instrument, wherein a quadrangular frame surrounds the trocar and includes a first subframe disposed in a horizontal direction, and a second subframe disposed in a vertical direction, contacting the first subframe, and the detecting the position information of the surgical instrument comprises detecting an X-coordinate and Y-coordinate of the surgical instrument in the trocar based on output values of a first photodiode array mounted in the first subframe and output values of a second photodiode array mounted in the second subframe.

16. The control method according to claim 15, wherein the controlling the operation of the robot comprises:

comparing the received position of the instrument with a predetermined reference range corresponding to a circumferential region about the instrument;

generating a control signal according to a result of the comparison; and transmitting the control signal to the robot to perform an operation using the instrument, wherein a diameter of the predetermined reference range is equal to or lesser than a diameter of a through-hole formed in the trocar.

17. The control method according to claim 16, wherein when a user inputs a command to the robotic system, the generating the control signal comprises:

generating a control signal according to the input command by maintaining the input command if the received position of the instrument is within the predetermined reference range, or generating a control signal according to the input command by modifying the input command if the received position of the instrument is on a boundary of the predetermined reference range or outside of the predetermined reference range.

18. The control method according to claim 17, wherein the modifying the input command includes one of stopping a motion of the robot, moving the robot by a distance less than a distance input by the user, or reducing a moving speed of the robot to a speed less than a speed input by the user.

19. A position detection apparatus comprising:

a frame configured to be coupled to a trocar, the frame including a first subframe disposed in a first direction, and a second subframe disposed in a second direction, contacting the first subframe;

a sensing unit comprising a first photodiode array mounted in the first subframe and a second photodiode array mounted in the second subframe;

a light-emitting unit comprising a first light-emitting unit mounted in a third subframe facing the first subframe to emit light to the first photodiode array and a second light-emitting unit mounted in a fourth subframe facing the second subframe to emit light to the second photodiode array;

a coordinate detection unit to detect an X-coordinate of an instrument inserted into the trocar based on output values of the first photodiode array and a Y-coordinate of the instrument inserted into the trocar based on output values of the second photodiode array; and a transmission unit to transmit the detected coordinate information.

20. The position detection apparatus of claim 19, wherein the frame is a polygonal frame.

21. The position detection apparatus of claim 19, wherein the frame is a circular frame, having a diameter equal to or greater than a diameter of the trocar.

* * * * *